United States Patent
Richtmyer et al.

(10) Patent No.: US 11,793,452 B2
(45) Date of Patent: Oct. 24, 2023

(54) METHOD OF VISUALIZING AND QUANTIFYING REMINERALIZATION

(71) Applicant: Johnson & Johnson Consumer Inc., Skillman, NJ (US)

(72) Inventors: Matthew Richtmyer, Pennington, NJ (US); Chantel Tester, Belle Mead, NJ (US); Daniel Queiroz, Belle Mead, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 406 days.

(21) Appl. No.: 17/061,432

(22) Filed: Oct. 1, 2020

(65) Prior Publication Data

US 2021/0100495 A1    Apr. 8, 2021

Related U.S. Application Data

(60) Provisional application No. 62/910,024, filed on Oct. 3, 2019.

(51) Int. Cl.
| | |
|---|---|
| *A61B 5/00* | (2006.01) |
| *G06T 11/20* | (2006.01) |
| *G06T 7/00* | (2017.01) |

(52) U.S. Cl.
CPC .......... *A61B 5/4547* (2013.01); *A61B 5/0075* (2013.01); *G06T 7/0012* (2013.01); *G06T 11/206* (2013.01); *G06T 2207/10064* (2013.01); *G06T 2207/30036* (2013.01)

(58) Field of Classification Search
CPC ... A61B 5/4547; A61B 5/0075; A61B 5/4833; A61B 5/0088; A61B 5/0071; G06T 7/0012; G06T 11/206; G06T 2207/10064; G06T 2207/30036; G01N 2021/646; A61K 6/25
See application file for complete search history.

(56) References Cited

U.S. PATENT DOCUMENTS

| | | | |
|---|---|---|---|
| 5,071,840 A | 12/1991 | Ebetino et al. | |
| 5,137,880 A | 8/1992 | Ebetino et al. | |
| 5,334,586 A | 8/1994 | Ebetino et al. | |
| 5,393,746 A | 2/1995 | Ebetino et al. | |
| 5,519,013 A | 5/1996 | Ebetino et al. | |
| 5,574,024 A | 11/1996 | Ebetino et al. | |
| 5,753,634 A | 5/1998 | Ebetino et al. | |
| 5,824,661 A | 10/1998 | Francis et al. | |
| 6,043,026 A | 3/2000 | Patchett et al. | |
| 6,121,253 A | 9/2000 | Han et al. | |
| 6,949,251 B2 | 9/2005 | Dalal et al. | |
| 7,514,594 B2 | 4/2009 | Askew et al. | |
| 7,749,953 B2 | 7/2010 | Bab et al. | |
| 7,796,243 B2 | 9/2010 | Choo-Smith et al. | |
| 7,833,968 B2 | 11/2010 | Soo et al. | |
| 8,293,477 B2 | 10/2012 | Glimcher et al. | |
| 8,951,505 B2 * | 2/2015 | Pashley ............... | A61K 6/838 |
| | | | 424/602 |
| 8,993,720 B2 | 3/2015 | Drezner et al. | |
| 9,271,808 B2 | 3/2016 | Teixeira et al. | |
| 2002/0119100 A1 * | 8/2002 | Okada ................ | A61K 6/65 |
| | | | 424/9.7 |
| 2003/0181374 A1 | 9/2003 | Mundy et al. | |
| 2007/0099822 A1 | 5/2007 | Rowe | |
| 2009/0047287 A1 | 2/2009 | Billiard et al. | |
| 2009/0181098 A1 | 7/2009 | Garrett et al. | |
| 2011/0038921 A1 | 2/2011 | Wen et al. | |
| 2012/0253470 A1 | 10/2012 | Guze et al. | |
| 2012/0301508 A1 | 11/2012 | Hsieh et al. | |
| 2012/0316241 A1 | 12/2012 | Toguchida | |
| 2015/0010878 A1 | 1/2015 | Seibel et al. | |
| 2015/0230889 A1 | 8/2015 | Kim | |
| 2015/0272983 A1 | 10/2015 | Hsieh et al. | |
| 2018/0243449 A1 | 8/2018 | Perfect et al. | |
| 2019/0328234 A1 * | 10/2019 | Seibel ............... | A61B 5/14539 |
| 2021/0169403 A1 * | 6/2021 | Bloembergen ....... | A61B 5/4547 |

FOREIGN PATENT DOCUMENTS

| | | | |
|---|---|---|---|
| AU | 2013 203 943 A1 | 5/2013 | |
| EP | 273514 B1 | 12/1990 | |

OTHER PUBLICATIONS

Graham Jasmine Y et al: "Optical measurement of acidification of human dental plaque in vitro," Progress in Biomedical Optics and Imaging, Spie—International Society for Optical Engineering, vol. 10473, Feb. 9, 2018, pp. 104730A-104730A, XP060100860.
D'Alpino, et al., "Use of fluorescent compounds in assessing bonded resin-based restorations: A literature review," Journal of Dentistry, vol. 34, No. 9, Oct. 1, 2006, pp. 623-634. XP005636398.
Generali Luigi, et al., "Double dye technique and fluid filtration test to evaluate early sealing ability of an endodontic sealer," Clinical Oral Investigations, vol. 21, No. 4, Jun. 14, 2016, pp. 1267-1276. XP036216166.
International Search Report, PCT/IB2020/059268; dated Dec. 9, 2020.

* cited by examiner

*Primary Examiner* — Tom Y Lu
(74) *Attorney, Agent, or Firm* — Darryl C. Little

(57) ABSTRACT

A method of assessing and/or quantifying remineralization in a tooth model by exposing a tooth model to calcium and a calcium-binding fluorophore either sequentially or simultaneously under conditions sufficient to produce a remineralized/demineralized tooth model; exposing the remineralized/demineralized tooth model to a non-calcium binding fluorophore to produce an enhanced tooth model; and assessing and/or quantifying remineralization, demineralization, or both on the enhanced tooth model by determining the location and extent of calcium binding fluorophore and non-calcium binding fluorophore on the enhanced test tooth sample.

10 Claims, No Drawings

METHOD OF VISUALIZING AND QUANTIFYING REMINERALIZATION

CROSS-RELATED APPLICATION

The present application claims the benefit of the earlier filing date of United States provisional patent application 62/910,024, filed Oct. 3, 2019, the entirety of which application is hereby incorporated by reference herein as if fully set forth herein.

FIELD OF THE INVENTION

The present invention relates to methods to assessing mineral gain and/or loss in teeth or a tooth model. More particularly, this invention relates to methods of assessing and/or quantifying remineralization and/or demineralization effect in a tooth models using calcium binding fluorophores and non-calcium binding fluorophores.

BACKGROUND OF THE INVENTION

Dental caries is caused by the action of acids on the enamel surface. The acid is produced when sugars (mainly sucrose) in foods or drinks react with bacteria present in the dental biofilm (plaque) on the tooth surface.

Dental caries may be characterized by the dissolution of apatite from the tooth. Generally, efficacy of anticaries treatments may be measured by methods such as fluoride uptake or change in surface microhardness. These methods, however, provide only an indirect measurement of mineral gain/loss. Interpretation of these results is further complicated by the fact that caries formation is a subsurface phenomenon, and these methods cannot easily distinguish between remineralization at the surface or deeper in the lesion. Imaging of tooth models with Transverse Micro Radiography (TMR) directly images the mineral density but does not distinguish between native mineral and mineral added following caries treatment.

In testing new formulations for efficacy in mineral gain/loss, distinguishing between native mineral and mineral added following treatment is crucial in determining formulation efficacy.

In summary, there are many methods to qualifying and quantifying dental caries and methods of their treatment. These methods lack in the ability to distinguish between remineralization at the surface or deeper in the lesion. What is needed is a new method to evaluate anticaries treatments by co-labeling mineralized and demineralized regions of enamel, and assessing, qualifying and/or quantifying efficacy of the treatment.

SUMMARY OF THE INVENTION

According to one aspect, the present invention provides methods of assessing and/or quantifying remineralization and/or demineralization in a tooth model comprising the steps of: (a) exposing a tooth model to calcium and a calcium-binding fluorophore either sequentially or simultaneously under conditions sufficient to produce a remineralized/demineralized tooth model; (b) exposing the remineralized/demineralized tooth model of step (a) to a non-calcium binding fluorophore to produce an enhanced tooth model; and (c) assessing and/or quantifying remineralization, demineralization, or both on the enhanced tooth model by determining the location and extent of calcium binding fluorophore and non-calcium binding fluorophore on the enhanced test tooth sample.

DETAILED DESCRIPTION OF THE INVENTION

Described is a method to assess and/or quantify mineral gain and/or loss in a tooth model. Using this method, various anticaries treatments may be evaluated and compared, including but not limited to, technical approaches that promote mineralization and/or prevent demineralization. In this method, mineralized and demineralized regions of enamel are co-labeled and imaged using confocal microscopy.

As used herein the term "tooth model" refers to (a) a tooth or teeth sample of an animal, including, e.g., one or more human, bovine, rat, porcine, ovine, caprine, equine, or other animal teeth, as well as, (b) a natural and/or synthetic material sample used to model the properties of a tooth or teeth, in particular a material sample that models the remineralization and/or demineralization properties of a tooth, e.g. a hydroxyapatite disk, calcium phosphate or other disks, and the like. Any suitable tooth model(s) may be used in accord with the present invention. In certain embodiments, the tooth model comprises one or more animal teeth, for example human teeth, bovine teeth, or a combination thereof. In certain preferred embodiments the tooth model comprises a human tooth. In certain other preferred embodiments the tooth model comprises a bovine tooth.

The tooth model used may have lesions therein, e.g. occurring naturally (created in vivo or in situ) or introduced artificially as described below. The tooth model used may have no lesions therein.

In certain embodiments, the tooth model used in the present methods has lesions introduced therein prior to the exposure to calcium. Any suitable method for creating lesions in the tooth sample may be used in accord with the present methods, for example, the enamel of the tooth specimen may be polished to provide a uniform surface and artificial lesions may be formed by exposure of the polished enamel surface to any number of acids. The acids may be in the form of solutions or gels or combinations thereof and the like. The acids used to create artificial lesions include lactic acid, citric acid, acetic acid, propionic acid, formic acid, succinic acid, butyric acid, hydrochloric acid, phosphoric acid, combinations of two or more thereof, and the like. The strength of the acid and the time of exposure will create a variety of artificial lesions in the tooth model. Other suitable methods for introducing lesions include electrophoresis and other methods known in the art.

The present invention may use any of a variety of methods for exposing the tooth model to both calcium and a calcium-binding fluorophore, either sequentially or simultaneously, under conditions sufficient to produce a tooth model having deposited thereon calcium that is loosely or firmly bound with said tooth model and that is associated with the calcium-binding fluorophore and which deposited calcium may be measured to determine remineralization and/or demineralization on the tooth model. For example, in certain embodiments, the tooth model may be exposed to a composition comprising calcium under conditions sufficient to deposit calcium, or precipitate a calcium salt, on to the tooth model. or under conditions sufficient to promote incorporation of calcium, or precipitate a calcium salt, into the tooth model and then subsequently be exposed to a calcium-binding fluorophore to associate the fluorophore with the deposited calcium/calcium salt for visualization. Alternatively, the tooth model may be exposed to calcium and calcium-binding fluorophore at the same time to both deposit calcium/calcium salt onto the tooth model and associate the calcium-binding fluorophore with the deposited calcium/calcium salt simultaneously or substantially simultaneously. Those of skill in the art will recognize that a variety of other combinations of compositions may be introduced to achieve the step of producing a remineralized/demineralized tooth model in accord with the present invention.

Any suitable source of calcium may be used to introduce and expose the tooth model to calcium. Suitable sources of calcium include, for example, saliva, artificial saliva, calcium chloride, calcium carbonate, calcium phosphate, tricalcium citrate, calcium lactate, calcium lactate gluconate, calcium gluconate. In addition, any suitable calcium-binding fluorophores may be used in accord with the present invention.

Examples of suitable calcium-binding fluorophores include calcein or any one following of the trademarked compounds: FLUO-3, FLUO-4, FLUO-5, FLUO-4 DIRECT, or MAG-FLUO-4 (AAT Bioquest, Inc., Sunnyvale Calif., USA). One or more of these calcium binding fluorophores may be available from ThermoFisher Scientific Company (Waltham, Mass., USA). In certain preferred embodiments, the calcium-binding fluorophore comprises calcein. The calcium binding fluorophores may be exposed to the tooth model in the form of a solution. Such solutions typically contain calcium, phosphate, or treatments to promote remineralization such as fluoride. The time of exposure of the tooth model to the calcium binding fluorophore may be from about one minute to about twenty hours, or from about thirty minutes to about twenty hours, or about twenty hours.

In certain embodiments, the step of exposing the tooth model to both calcium and a calcium-binding fluorophore to produce a remineralized/demineralized tooth model comprises exposing the tooth model to calcium, a calcium-binding anion, and a calcium-binding fluorophore under conditions sufficient to precipitate the calcium and calcium-binding anion as a calcium salt on to or into the tooth model to achieve mineralization thereof. Any of a variety of anions and calcium salts may be used in accord with the present invention. Examples of suitable anions include phosphate, oxalate, fluoride, carbonate, hydroxide, combinations of two or more thereof and the like which result, respectively, in the deposition of calcium salts such as calcium phosphate, calcium oxalate, calcium fluoride, calcium carbonate, calcium hydroxide combinations of two or more thereof and the like on to or into the tooth model. As described above, the calcium-binding fluorophore may be introduced at any time suitable to associate the fluorophore with the calcium in the calcium salt that is, or has been, deposited on the tooth.

Exposure to the calcium and optional calcium-binding anion to achieve remineralization may be for any suitable time. For example, the remineralization time may be greater than 24 hours, or from about five minutes to about twenty-four hours, or from about one hour to about twelve hours, or about one hour.

According to certain embodiments, the present methods include the step of treating the tooth model with an oral care composition prior to or post exposing the tooth model to calcium, calcium-binding fluorophore and optional calcium-binding anion in order to measure the effect of the oral care composition on the remineralization or demineralization, for example, the effect if any on the localization of remineralization on the tooth model, the depth and extent of remineralization, and/or demineralization. Any suitable oral care composition may be tested including compositions in the form of a dentifrice, toothpaste, leave-on gel, powder, mouthwash, concentrate, strip, gum, and any combinations of two or more of the above. Treatment of the tooth model with the oral care composition is done for a treatment contact time. The treatment contact time may include, for example, a time of from about thirty seconds to about four hours, or from about thirty seconds to about thirty minutes, or from about one minute to about ten minutes, or from about one minute to about five minutes, or about one minute.

In some embodiments, the tooth model treatment with an oral care composition and remineralization are performed one time. In other embodiments, multiple treatments and/or remineralizations are repeated two times, or four times, or twenty times, or forty times, or sixty times. The purpose of multiple treatments and/or remineralizations is to understand the cumulative effect of multiple treatments on remineralization efficacy. In other embodiments, the tooth model treatment and remineralization are performed one or multiple times a day for more than one day. The number of days of treatment and remineralization may be one day, or three days, or five days, or ten days, or twenty days, or thirty days or more. The purpose of multiple days of treatments and/or remineralizations is to simulate extended product usage, and understand the cumulative effect of multiple treatments over time.

In some embodiments, the tooth model may be exposed to at least one demineralization composition for at least one demineralization time. Demineralization compositions are known to dissolve calcium apatite from the surface of the enamel. Such solutions typically contain acids, and may also contain calcium, phosphate, chelating agents or other salts. The purpose of one or more demineralization and/or remineralizations is to simulate the daily changes in oral pH that occur with eating or drinking, and to understand the effect of the treatment on preventing demineralization and/or promoting remineralization.

The demineralization time may be from about one minute to about four hours, or from about five minutes to about four hours, or about four hours.

In some embodiments, the tooth model treatment, remineralization, and demineralization steps are performed one time. In other embodiments, they may be repeated two times, or four times, or twenty times, or forty times, or sixty times. The purpose of multiple treatments and/or remineralizations is to understand the cumulative effect of multiple treatments. In other embodiments, the tooth model treatment, remineralization, and demineralization steps are performed one or multiple times a day for more than one day. The number of days of treatment, remineralization, and demineralization may be one day, or three days, or five days, or ten days, or twenty days, or thirty days or more. The purpose of multiple days of treatments and/or remineralizations is to simulate extended product usage, and understand the cumulative effect of multiple treatments over time.

In some embodiments the tooth model may be exposed to cycling steps sufficient to yield a net mineralization effect. In some embodiments the tooth model may be exposed to cycling steps sufficient to yield a net demineralization effect.

According to the present invention, the tooth model is exposed to a composition that comprises a second, non-calcium binding, fluorophore that labels regions of the enamel that remain demineralized after treatment to produce an enhanced tooth model. This fluorophore should be able to diffuse into the demineralized lesion, and have fluorescence excitation and emission spectra that are at least partially distinct from that of the calcium-binding fluorophore. One example is the use of rhodamine in combination with the calcium binding fluorophore, calcein. Examples of a rhodamine suitable are rhodamine B, rhodamine WT, and sulforhodamine B. One or more of these rhodamines may be available from Sigma-Aldrich.

The non-calcium binding fluorophore may be exposed to the tooth model in the form of a solution. The time of exposure may be from about one minute to about twenty-four hours, or from about five minutes to about six hours, or about one hour.

After the above steps have been performed, the demineralization and/or remineralization of the tooth model may be assessed and/or quantified by measuring the fluorescence light emitted from the calcium binding fluorophore and the non-calcium binding fluorophore. Any suitable methods of measuring fluorescence may be used for assessing and/or quantifying fluorescent light in this method of the present invention. Suitable methods for measuring fluorescence include, but are not limited to, measurements obtained from a fluorometer, including filter fluorometers or spectrofluorometer. In certain embodiments, the measurements can, then, be assessed to determine the existence and/or relative (as opposed to quantified) extent of calcium binding fluorophores and/or non-calcium binding fluorophores.

In certain embodiments, the methods of the present invention comprise measuring and generating an image of at least a portion of a fluorescently labelled remineralized/demineralized tooth model using a proper imaging technique, e.g. a confocal laser scanning microscope, for further assessment by visualizing and/or quantifying the extent and/or localization of the demineralization and/or remineralization. For example, as further described below, the fluorescently labelled remineralized/demineralized tooth model specimens from Example I were sectioned longitudinally through the lesions, mounted in epoxy resin so that the cut surface was exposed, and serially polished. The enamel cross-sections were then imaged using a Leica TCS SP5 upright confocal laser scanning microscope. Fluorescence from calcein was excited using the 488 nm line of Argon and emission intensity measured from 505-530 nm. Fluorescence from rhodamine-PE was excited using the 543 nm line of HeNe and emission intensity measured from 570-620 nm.

In certain embodiments, measuring, assessment and/or quantifying fluorescent light may be performed at the tooth model surface, which will quantify the proportion of loose calcium (i.e. calcium deposited onto the surface). In other embodiments, measuring assessment and/or quantifying fluorescent light may be performed subsurfacely. For example, depths below the tooth model surface may be measured directly (e.g. confocal imaging) or the tooth model may be cut into a cross-section, transverse section, sagittal section etc. and then measured. The measurement and quantification will quantify the proportion of firmly bound calcium (i.e. calcium incorporated into the tooth model structure). In other embodiments, measuring, assessment and/or quantifying fluorescent light may be performed at both the tooth model surface and subsurface which will determine the relative proportions of loosely to firmly bound calcium.

The resulting images can be analyzed using image analysis software. Image analysis can identify target surfaces within the area of the lesion (e.g. surface/subsurface remineralization bands and demineralization bands) as well as quantify features, including such as area. Examples of image analysis software which could be used includes ImageJ/FIJI, Python using libraries such as OpenCV, Mahotas, Scikit-image, Scipy, and TensorFlow, and MATLAB (Matrix Laboratory).

Images can be prepared for analysis by using a normalization step to control for variability (including biological variability and acquisition variability). The images can then be pre-processed to remove aberrations/artifacts using routines like inverse frequency filtering (e.g. inverse Fourier Transforms). Then, the images are segmented. Common examples of segmentation include binarization by using a pixel intensity threshold (e.g. Otsu's Method), Watershed Segmentation, Region Growing and K-Means Clustering. Once the image is segmented and binarized, parameters like region counting, region area and edge/boundary morphologies can be calculated.

The quantified images may be used to compare the remineralization efficacy of oral care compositions. In studies, these results could be compared to negative controls, such as treatment with deionized water (D.I.), or to positive controls, such as treatment with fluoride solutions.

Other suitable methods for visualizing and quantifying the demineralization and/or remineralization of the tooth model in accord with the present invention include Raman spectroscopy, time of flight secondary ion mass spectrometry, parsing individual rows and/or column vectors out of an image, and the like.

In addition, methods may include changing dimensionality from the images captured from fluorescent imaging. Currently, a $m \times n \times o$ matrix is used for computations, where m corresponds to rows of the matrix, n corresponds to columns of the matrix, and the third variable o corresponds to the image stack height. In the present calculations, $o=3$, corresponding to the RGB color space, and m, and n correspond to the height and width of the images respectively. Dimensionality could be reduced to an $m \times n \times 2$ matrix, by reducing an image stack (e.g. the Blue stack, as the fluorophores signal strongly in the Red and Blue spaces) or through image compression. Similar segmentation algorithms could be used as described previously to segment target regions (e.g. threshold segmentation, region-growing, clustering). Dimensionality could be reduced to a $m \times n \times 1$ matrix, or a grayscale image. Similar segmentation algorithms could be used to segment target regions and identify the localization of target surfaces. Also, dimensionality could also be reduced to a $m \times 1$ or a $1 \times n$ vector. These vectors could be chosen arbitrarily, through taking the average/mean of neighboring row/column vectors, etc. A sufficiently large change in pixel intensity difference within these vectors will correspond to an edge (i.e. target surface). The corresponding index at the edges can be used to calculate the depth within the sample that the surface occurred at.

EXAMPLES

Example I

Specimen Preparation and Treatment Regimen

Human enamel specimens were polished and artificial lesions formed by immersion into a solution of 0.1 M lactic acid and 0.2% Carbopol C907 which was 50% saturated with hydroxyapatite and adjusted to pH 5.0. The average specimen surface microhardness (SMH) was determined from four indentations on the surface of each specimen, using a Vickers hardness indenter at a load of 200 g for 15 seconds. The lesion surface hardness range was 25-45 VEIN and average lesion depth was approximately 70 μm. Treatment groups were created by dividing specimens into subgroups balanced by post-lesion surface microhardness (SMH) values.

Remineralization efficacy was evaluated by treatment consisting of a four hour/day acid challenge in the lesion forming solution and four, one-minute mouth rinse treatment periods. The remaining time (~twenty hours) the specimens were in artificial saliva containing 2.2 g/L gastric mucin, 0.381 g/L sodium chloride, 0.213 g/L of calcium chloride dihydrate, 0.738 g/L of potassium phosphate monobasic, 1.114 g/L of potassium chloride, and 25 ppm of calcein. The treatment schedule used for this experiment is given in Table 1.

TABLE 1

Daily pH cycling regimen.

| | Time | Event | Description |
|---|---|---|---|
| a) | 8:00-8:01 a.m. | Treatment #1* | 5 second DI rinse, Soak in test product for 1 min |
| b) | 8:01-9:00 a.m. | Remin | Soak in artificial saliva for 1 hour |
| c) | 9:00-9:01 a.m. | Treatment #2 | 5 second DI rinse, Soak in test product for 1 min |
| d) | 9:01-10:00 a.m. | Remin | Soak in artificial saliva for 1 hour |
| e) | 10:00 a.m.-2:00 p.m. | Demin | 5 second DI rinse, acid challenge in lesion forming solution for 4 hours |
| f) | 2:01-3:00 a.m. | Remin | Soak in artificial saliva for 1 hour |
| g) | 3:00-3:01 p.m. | Treatment #3 | 5 second DI rinse, Soak in test product for 1 min |
| h) | 3:01-4:00 a.m. | Remin | Soak in artificial saliva for 1 hour |
| i) | 4:00-4:01 p.m. | Treatment #4 | 5 second DI rinse, Soak in test product for 1 min |
| j) | 4:01 p.m.-8:00 a.m. | Remin | Soak in artificial saliva overnight |
| k) | Back to (a) | | |

*On the first day, this treatment will be preceded by one hour in the artificial saliva prior to any treatments.

The test product used in the evaluation was a 100 ppm solution of fluoride in DI water (100 ppm F). As a negative control, the "test product" used was DI water (a 0 ppm solution of fluoride, or 0 ppm F). The regimen was repeated for time periods of 5, 10 and 20 days. At each time period (5, 10, 20 days), six specimens from each group were removed from pH cycling and stained for one hour by immersion in 1 wt % aqueous solution of rhodamine B.

Example II

Imaging Procedure

The treated enamel specimens from Example I were sectioned longitudinally through the lesions, mounted in epoxy resin so that the cut surface was exposed, and serially polished. The enamel cross-sections were then imaged using a Leica TCS SP5 upright confocal laser scanning microscope. Fluorescence from calcein was excited using the 488 nm line of Argon and emission intensity measured from 505-530 nm. Fluorescence from rhodamine-PE was excited using the 543 nm line of HeNe and emission intensity measured from 570-620 nm.

Example III

Qualitative Analysis

Following the specimen preparation and treatment regimen outlined in Example I and the imaging procedure of Example II, the confocal images of cross-sectioned enamel specimens treated with 0 ppm fluoride (0 ppm F) or 100 ppm fluoride (100 ppm F) solutions for twenty days were compared. For specimens treated with 0 ppm F, only a thin, weak band of calcein fluorescence was visible at the base of the lesion, corresponding to the mineral that has been added over the course of treatment and pH cycling. Treatment with 100 ppm F results in two intense bands of calcein fluorescence at the base and surface of the lesion, suggesting that remineralization has occurred in two discrete locations. In the corresponding images of rhodamine B fluorescence, specimens treated with zero ppm F show rhodamine penetration throughout the body of lesion, confirming minimal remineralization. In specimens treated 100 ppm F rhodamine B fluorescence is seen primarily at the enamel surface, suggesting that remineralization of the lesion surface inhibits diffusion deeper into the lesion body.

Example IV

Qualitative Analysis

Image analysis was performed using MATLAB R2017a version 9.2.0.55.6344. with the Image processing Toolbox (Version 10.0, R2017a release) and Statistics and Machine Learning Toolbox (Version 11.1, R2017a release).

User defined functions were created using a K-means clustering routine. Input RGB images were converted to the L*a*b* color space. The a* and b* color planes were segmented into 3 clusters, corresponding to the rhodamine signal, calcein signal, and the background. Segmented regions were converted to binary masks using Otsu's method of binarization. Morphological operators were used to decrease salt-and-pepper noise and the area was calculated using a weighted sum of the pixels (i.e. bwarea MATLAB function). Each image was then normalized to control for biological variability of the lesion and to calculate the proportion of calcein to rhodamine signal in a given image.

This method allows for the quantitative extraction of approximately unique (i.e. mutually exclusive) target areas. Therefore, parameters can be normalized per sample controlling for variability and allowing for comparison between groups.

Table 2 shows the proportion of calcein signal to rhodamine signal for specimens prepared and treated as described in Example I for 20 days with 0 ppm fluoride (0 ppm F) or 100 ppm fluoride (100 ppm F) solutions for twenty days.

TABLE 2

Calcein/rhodamine signal proportions after 20 days of treatment

| ppm fluoride | Calcein proportion | Rhodamine proportion |
|---|---|---|
| 0 | 10.73 | 89.26 |
| 100 | 90.91 | 9.08 |

The table shows that treatment with 100 ppm F solution for twenty days dramatically increases the proportion of Calcein signal in the image, which is a result of a greater degree of remineralization when compared to treatment with 0 ppm F solution.

Table 3 shows the proportion of calcein signal to rhodamine signal for specimens prepared and treated as described in Example I with 100 ppm fluoride (100 ppm F) solutions for five days versus ten days.

TABLE 3

Calcein/rhodamine signal proportions with 100 ppm F treatment

| Time (days) | Calcein proportion | Rhodamine proportion |
|---|---|---|
| 5 | 23.53 | 76.46 |
| 10 | 96.54 | 3.45 |

The table shows that treatment with 100 ppm F solution for ten days dramatically increases the proportion of Calcein signal in the image when compared to treatment with 100 ppm F solution for five days.

In testing new formulations for efficacy in mineral gain/loss, the methods described above may be used to compare the new treatment to a negative control (0 ppm F solution), as well as to a positive control (100 ppm F solution).

What is claimed is:

1. A method of assessing remineralization and/or demineralization in a tooth model comprising the steps of:
   (a) exposing a tooth model to calcium and a calcium-binding fluorophore comprising calcein, either sequentially or simultaneously, under conditions sufficient to produce a remineralized/demineralized tooth model;
   (b) exposing the remineralized/demineralized tooth model of step (a) to a non-calcium binding fluorophore comprising sulforhodamine B and/or at least one rhodamine to produce an enhanced tooth model; and
   (c) assessing remineralization, demineralization, or both on the enhanced tooth model by determining the presence, location and/or relative magnitude of the calcium binding fluorophore and the non-calcium binding fluorophore on the enhanced tooth model.

2. The method of claim 1 wherein said assessing step (c) comprises determining the location of calcium binding fluorophore and non-calcium binding fluorophore on the enhanced tooth model.

3. The method of claim 1 wherein said assessing step (c) comprises visualizing and quantifying the remineralization, demineralization, or both by measuring fluorescence light emitted from the calcium binding fluorophore and the non-calcium binding fluorophore and creating an image based thereon.

4. The method of claim 3 wherein said tooth model comprises a human or bovine tooth.

5. The method of claim 4 wherein said tooth model has natural or artificial lesions formed therein.

6. The method of claim 1 wherein said exposing step (a) comprises exposing said tooth model to an oral care composition followed by exposing said tooth model to calcium and a calcium-binding fluorophore under remineralization conditions to measure the effect of the oral care composition on remineralization on the tooth model.

7. The method of claim 1 wherein said exposing step (a) comprises exposing the tooth model to demineralization conditions sufficient to produce a demineralized tooth model.

8. The method of claim 1 wherein said exposing step (a) comprises exposing the tooth model to both remineralization and demineralization conditions.

9. The method of claim 1 wherein said assessing step (c) comprises visualizing remineralization, demineralization, or both using time of flight secondary ion mass spectrometry.

10. The method of claim 1 wherein said assessing step (c) comprises visualizing remineralization, demineralization, or both by parsing individual rows and/or column vectors out of an image.

* * * * *